US008970685B2

(12) United States Patent
Minetoma et al.

(10) Patent No.: US 8,970,685 B2
(45) Date of Patent: Mar. 3, 2015

(54) ENDOSCOPE APPARATUS

(75) Inventors: Yasuhiro Minetoma, Kanagawa (JP);
Hiroshi Yamaguchi, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 402 days.

(21) Appl. No.: 13/305,864

(22) Filed: Nov. 29, 2011

(65) Prior Publication Data

US 2012/0147166 A1    Jun. 14, 2012

(30) Foreign Application Priority Data

Dec. 13, 2010    (JP) ................. 2010-276915

(51) Int. Cl.
*A61B 1/00*    (2006.01)
*H04N 1/00*    (2006.01)
(Continued)

(52) U.S. Cl.
CPC ........... *A61B 1/0661* (2013.01); *A61B 1/00009* (2013.01); *A61B 1/043* (2013.01);
(Continued)

(58) Field of Classification Search
CPC .... A61B 1/00; A61B 1/0646; A61B 1/00163; G01N 2201/00; G02B 7/28; G03B 1/00; G03B 7/00; G03B 9/00; G03B 15/00; G03B 19/00; H04N 1/00
USPC ............. 348/45, 65, 72, 164, 223.1; 385/117; 396/17; 600/101; 386/279; 362/293; 382/232; 313/501; 345/102
See application file for complete search history.

(56) References Cited

U.S. PATENT DOCUMENTS 5,187,572 A    2/1993    Nakamura et al.
5,644,674 A *   7/1997    Aihara et al. ................. 386/279
(Continued)

FOREIGN PATENT DOCUMENTS

EP    1258220 A2    11/2002
EP    2020202 A2    2/2009
(Continued)

OTHER PUBLICATIONS

Stinson, Light Source: Working with Mixed Lighting, Oct. 1, 2003, Videomaker, p. 1-3.*

(Continued)

*Primary Examiner* — Sath V Perungavoor
*Assistant Examiner* — Albert Kir
(74) *Attorney, Agent, or Firm* — Birch, Stewart, Kolasch & Birch, LLP

(57) ABSTRACT

An endoscope apparatus is provided for which a user does not need to adjust irradiation light quantity intentionally while confirming a captured image. A captured image which is bright and has stable tint can be obtained without being limited by an imaging distance with respect to the observation of the structure or components of living bodies. The endoscope apparatus includes a first light source section, a second light source section, a light source control unit which controls the irradiation and irradiation light quantity, an imaging unit which obtains a captured image, luminance value calculating unit which calculates the luminance value, a light source light quantity changing unit which changes the irradiation light quantity according to the luminance value, a white balance adjustment value calculating unit which calculates a white balance adjustment value, and a gain adjusting unit which adjusts the gain of the imaging unit.

9 Claims, 8 Drawing Sheets

(51) Int. Cl.
  *A61B 1/06* (2006.01)
  *A61B 1/04* (2006.01)
  *A61B 1/045* (2006.01)
  *A61B 5/00* (2006.01)

(52) U.S. Cl.
  CPC .............. *A61B 1/045* (2013.01); *A61B 1/0638* (2013.01); *A61B 1/0646* (2013.01); *A61B 1/063* (2013.01); *A61B 1/0653* (2013.01); *A61B 5/686* (2013.01)
  USPC ............... 348/65; 348/68; 348/69; 348/70; 385/117; 606/46

(56) References Cited

U.S. PATENT DOCUMENTS

| | | | |
|---|---|---|---|
| 6,791,606 B1 * | 9/2004 | Miyano | 348/223.1 |
| 2003/0142496 A1 * | 7/2003 | Bloom et al. | 362/293 |
| 2004/0122291 A1 | 6/2004 | Takahashi | |
| 2004/0215060 A1 | 10/2004 | Ueno et al. | |
| 2007/0009162 A1 * | 1/2007 | Endo | 382/232 |
| 2007/0070216 A1 | 3/2007 | Yabe | |
| 2009/0167149 A1 * | 7/2009 | Ito | 313/501 |
| 2009/0289200 A1 | 11/2009 | Ishii | |
| 2010/0039368 A1 * | 2/2010 | Kim et al. | 345/102 |
| 2010/0265321 A1 | 10/2010 | Minai et al. | |
| 2012/0026339 A1 * | 2/2012 | Kojima et al. | 348/164 |

FOREIGN PATENT DOCUMENTS

| | | |
|---|---|---|
| EP | 2384688 A1 | 11/2011 |
| JP | 2006-68321 A | 3/2006 |

OTHER PUBLICATIONS

Hsu, Light Mixture Esitmation for Spatially Varying White Balance, Feb. 5, 2009, p. 1-8.*
Chinese Office Action and English translation thereof, dated Mar. 4, 2014, for Chinese Application No. 201110402416.2.

* cited by examiner

FIG. 4

| LIGHT QUANTITY RATIO (405LD:445LD) | COLOR CONVERSION COEFFICIENT TABLE | | |
|---|---|---|---|
| | KR | KG | KB |
| 100 : 0 | R0 | G0 | B0 |
| 90 : 10 | R10 | G10 | B10 |
| ⋮ | ⋮ | ⋮ | ⋮ |
| 50 : 50 | R50 | G50 | B50 |
| ⋮ | ⋮ | ⋮ | ⋮ |
| 10 : 90 | R90 | G90 | B90 |
| 0 : 100 | R100 | G100 | B100 |

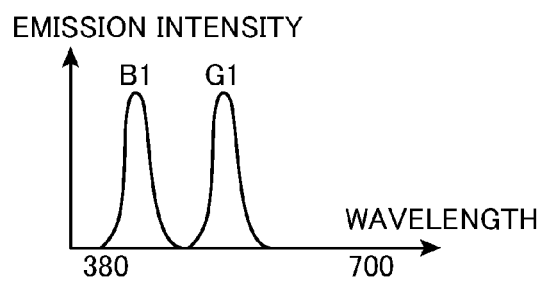
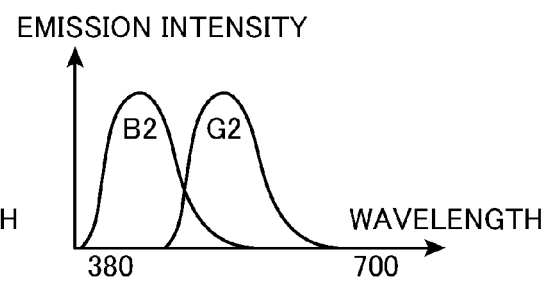
FIG. 8A
FIG. 8B

ENDOSCOPE APPARATUS

BACKGROUND OF THE INVENTION

The present invention relates to an endoscope apparatus which can perform special light observation using broadband light, such as white illumination light, and specific narrowband light.

In recent years, an endoscope apparatus which can perform so-called special light observation which irradiates specific narrow wavelength band light (narrowband light) onto a mucosal tissue of a living body and acquires tissue information at a desired depth of the body tissue is utilized. This type of endoscope apparatus can simply visualize living body information which is not acquired in, for example, normal observation images, such as enhancement of the surface layer fine structure of a new blood vessel generated in a mucosal layer or a submucosal layer, and a lesional part. For example, when an observation target is a cancerous lesional part, a fine blood vessel of a tissue surface layer or the state of fine structure can be observed in more detail if blue (B) narrowband light is irradiated on a mucosal tissue. Therefore, the lesional part can be more exactly diagnosed.

Even in this special light observation as well as the normal light (broadband light) observation, it is necessary to perform white balance processing on an acquired captured image in order to stabilize the reproducibility of color tone and to perform more exact diagnosis.

JP 2006-68321 A discloses an endoscope apparatus which can perform white balance processing in a short time in the normal light observation and the special light observation, respectively.

In the special light observation, when the distance between a diseased tissue and the irradiation position of the special light is short, a fine blood vessel or fine structure of a tissue surface layer which can be brightly viewed without difficulty can be imaged. However, there is a problem in that, as the distance increases, a captured image becomes dark and is not easily seen. Generally, a measure for increasing irradiation light quantity is taken. However, there is a limit to an increase in the irradiation light quantity, particularly, an increase in the light quantity of special light. There is a problem in that, if an attempt to compensate for the shortage of the light quantity of special light with normal light is made, the tint of a captured image changes.

SUMMARY OF THE INVENTION

An object of the invention is to provide an endoscope apparatus in which a user does not need to adjust irradiation light quantity intentionally while confirming a captured image in both of normal light observation and special light observation, and a captured image which is bright and has stable tint can always be obtained without being limited by an imaging distance with respect to the observation of the structure or components of living bodies, such as a surface layer fine blood vessel.

In order to achieve the above-mentioned objects, the resent invention provides an endoscope apparatus comprising:

a first light source section that irradiates first narrowband light with a predetermined wavelength bandwidth narrowbanded according to the spectral characteristics of the structure or components of a living body used as an object;

a second light source section that irradiates second narrowband light with a wavelength band different from the first narrowband light or broadband light with a broad wavelength band including visible light;

a light source control unit which controls the irradiation and irradiation light quantity of the first narrowband light from the first light source section, and the irradiation and irradiation light quantity of the second narrowband light or broadband light from the second light source section, respectively;

an imaging unit which obtains a captured image of the object to output captured image information, using return light from the object, of the first narrowband light and the second narrowband light or broadband light sequentially or simultaneously irradiated to the object;

a luminance value calculating unit which calculates the luminance value of the captured image from the captured image information imaged by the imaging unit;

a light source light quantity changing unit which changes the irradiation light quantity of the first narrowband light from the first light source section, and the irradiation light quantity of the second narrowband light or broadband light from the second light source section, according to the luminance value calculated in the luminance value calculating unit;

a white balance adjustment value calculating unit which calculates a white balance adjustment value for taking the white balance of the captured image from the irradiation light quantities, changed in the light source light quantity changing unit, of the first light source section and the second light source section which perform irradiation currently; and a gain adjusting unit which adjusts the gain of the imaging unit so that the white balance of the captured image becomes a basis white balance according to the white balance adjustment value calculated in the white balance adjustment value calculating unit.

Further, preferably, the basis white balance is a white balance of the captured image obtained when a white plate is imaged with the irradiation light quantity of the first light source section and the irradiation light quantity of the second light source section being maximized, respectively.

Further, preferably, the light source light quantity changing unit is the unit which changes the ratio of the irradiation light quantity of the first narrowband light from the first light source section and the irradiation light quantity of the second narrowband light from the second light source section; and the light source light quantity changing unit is the unit which changes the ratio of the irradiation light quantity of the first narrowband light from the first light source section and the irradiation light quantity of the broadband light from the second light source section.

Further, preferably, the light source light quantity changing unit increases the ratio of the irradiation light quantity from the first light source section as the calculated luminance value becomes large, and increases the ratio of the irradiation light quantity from the second light source section as the calculated luminance value becomes small, thereby setting the calculated luminance value to a predetermined luminance value.

Further, preferably, the light source light quantity changing unit gradually changes the irradiation light quantity of the first narrowband light from the first light source section according to the luminance value of the captured image; and the light source light quantity changing unit continuously changes the irradiation light quantity of the first narrowband light from the first light source section according to the luminance value of the captured image.

Further, preferably, if the basis white balances are [R_base, G_base, B_base], the ratio of the irradiation light quantity of the first light source section and the irradiation light quantity of the second light source section is $\alpha:1-\alpha$, the white balances of the first light source section are [R_1, G_1, B_1], and the white balances of the second light source section are [R_2, G_2, B_2], the gains [WB_gainR, WB_gainG, WB_gainB] of the imaging element adjusted by the gain adjusting unit are expressed by the following formulas.

$$WB\_gainR=(\alpha R\_1+(1-\alpha)R\_2)/R\_base$$

$$WB\_gainG=(\alpha G\_1+(1-\alpha)G\_2)/G\_base$$

$$WB\_gainB=(\alpha B\_1+(1-\alpha)B\_2)/B\_base$$

The present invention also provides an endoscope apparatus, further comprising:

an image processing section which performs predetermined image processing on the captured image information,
wherein the image processing section has a color conversion coefficient table showing the relationship between the ratio of the irradiation light quantity of the first light source section and the irradiation light quantity of the second light source section which are obtained in advance, and a color conversion coefficient for adjusting the tint of the captured image so that image processing is performed, and thereby, the white balance of the captured image does not change, and
wherein the image processing section selects the color conversion coefficient from the color conversion coefficient table on the basis of the ratio of the irradiation light quantity of the first light source section and the irradiation light quantity of the second light source section adjusted by the light source light quantity changing unit.

Further, preferably, the first light source section includes a broadband light source which emits broadband light, and a first color filter which transmits only the first narrowband light from the broadband light emitted from the broadband light source;

the second light source section includes the broadband light source and a second color filter that transmits only the second narrowband light from the broadband light emitted from this broadband light source; and the light source light quantity changing unit is the unit which switches at least one of the first color filter and the second color filter to a color filter with a different half-value width.

According to the endoscope apparatus of the invention, the light emission conditions of the special light source and the white illumination light source are controlled in order so that the light quantity of the return light detected with the imaging element always becomes equal to or more than a predetermined value in the normal light observation and the special light observation. Additionally, when normal light observation and special light observation are performed in order to perform predetermined image processing for adjusting tint in the image processing section according to the light emission conditions of the special light source and the white illumination light source, for example, even if imaging is performed apart from a lesional part or even if imaging is performed close to a lesional part, a user does not need to adjust the light emission conditions of the light sources and the tint of a captured image intentionally while confirming the captured image, and a captured image which has stable tint can always be obtained without being limited by an imaging distance, particularly, in the special light observation of a lesional part, a surface layer fine blood vessel, or the like as well as in the normal light observation.

BRIEF DESCRIPTION OF THE DRAWINGS

FIG. 4 is a graph showing one example of a color conversion table provided in a special light color conversion section of a special light image processing section shown in FIG. 3.

FIG. 8A is graph showing an example of the spectral characteristics of a blue filter with a narrow half-value width which is the first color filter and a green filter with a narrow half-value width which is the second color filter, and FIG. 8B is a graph showing an example of the spectral characteristics of a blue filter with a wide half-value width which is the first color filter, and a green filter with a wide half-value width which is the second color filter.

DETAILED DESCRIPTION OF THE INVENTION

An endoscope apparatus of the invention will be described below in detail on the basis of preferred embodiments shown in the accompanying drawings.

Figure 1:
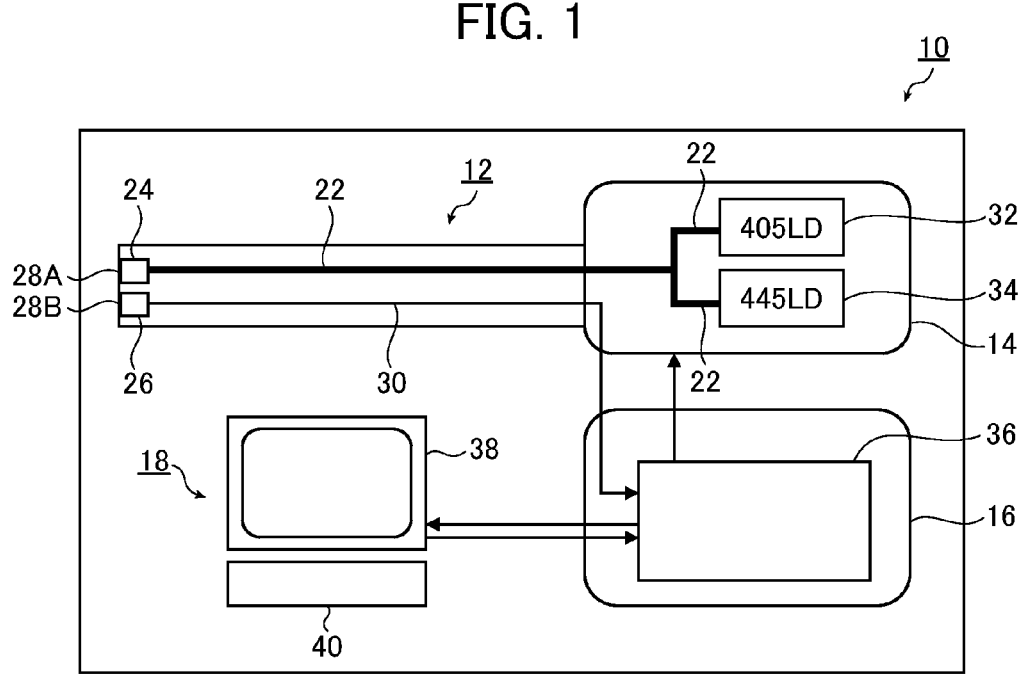
FIG. 1 is a block diagram schematically showing the overall configuration of a first embodiment of an endoscope apparatus of the invention.

FIG. 1 is a block diagram schematically showing the overall configuration of a first embodiment of the endoscope apparatus of the invention.

As shown in this drawing, the endoscope apparatus 10 of the invention has an endoscope 12, a light source device 14, a processor 16, and an input and output section 18. Here, the light source device 14 and the processor 16 constitute a control device of the endoscope 12, and the endoscope 12 is optically connected to the light source device 14, and is electrically connected to the processor 16. Additionally, the processor 16 is electrically connected to the input and output section 18. The input and output section 18 has a display section (monitor) 38 which displays image information or the like as output, a recording section (recording device) 42 (refer to FIG. 3) which outputs image information or the like, and an input section (mode switching section) 40 which functions as UI (user interface) which receives input operations, such as mode switching between a normal observation mode (also referred to as a normal light mode) and a special light observation mode (also referred to as a special light mode), and function settings.

The endoscope 12 is an electronic endoscope which has an illumination optical system which irradiates illumination light from the distal end thereof, and an imaging optical system which images a region to be observed. In addition, although not shown, the endoscope 12 includes an endoscope insertion part inserted into a subject, a manipulation part which performs curving manipulation of the distal end of the endoscope insertion part, and manipulation for observation, and connector parts which detachably connect the endoscope 12 to the light source device 14 and the processor 16 of the control device. Moreover, although not shown, various channels, such as a forceps channel which allows a treatment tool or the like for tissue sampling to be inserted thereinto, and air supply and water supply channels, are provided inside the manipulation part and the endoscope insertion part.

As shown in FIG. 1, a fluorescent body 24, though the details thereof will be described below, which constitutes the illumination optical system and constitutes a white light source, is provided in an irradiation port 28A which allows light to be irradiated to a region to be observed therethrough, at the distal end portion of the endoscope 12. An imaging element (sensor) 26, such as a CCD (Charge Coupled Device) image sensor or a CMOS (Complementary Metal-Oxide Semiconductor) image sensor serving as an imaging unit which acquires the image information of a region to be observed, are arranged at a light-receiving part 28B adjacent to the irradiation port 28A. A cover glass or a lens (not shown) which constitutes the illumination optical system is arranged at the irradiation port 28A of the endoscope 12, a cover glass or a lens (not shown) which constitutes the illumination optical system is arranged at the light-receiving part 28B, and an objective lens unit (not shown) which constitutes the imaging optical system is arranged at a light-receiving surface of the imaging element 26 of the light-receiving part 28B.

The endoscope insertion part is made curvable by the manipulation of the manipulation part, can be curved in arbitrary directions and at arbitrary angles according to parts of a subject in which the endoscope 12 is used, and can direct the irradiation port 28A and the light-receiving part 28B, that is, the observation direction of the imaging element 26, to a desired observation part.

In addition, although it is preferable that the imaging element 26 be a color imaging sensor or a complementary-color sensor including a color filter (for example, an RGB color filter or a complementary-color filter) in a light-receiving region, the RGB color imaging sensor is more preferable.

The light source device 14 includes as light-emitting sources, a blue-violet laser light source (405LD) 32 with a central wavelength of 405 nm which is used as a special light source in the special light mode, and a blue laser light source (445LD) 34 with a central wavelength of 445 nm which is used as a light source for white illumination light in both the normal light mode and the special light mode. The blue-violet laser light source 32 irradiates a blue-violet laser beam as first narrowband light, and the blue laser light source 34 irradiates a blue laser beam as second narrowband light. In addition, since the blue-violet laser beam with a central wavelength of 405 nm from the blue-violet laser light source 32 is narrowband light with a wavelength bandwidth which is narrow-banded according to the spectral characteristics of the structure or components of a living body, preferably, in conformity with the characteristics, the detectability of the structure or components of the living body is excellent.

The light emitted from a semiconductor light-emitting element of each of the light sources 32 and 34 is individually controlled by a light source control unit 48 (refer to FIG. 3), and the light emission conditions of each of the light sources 32 and 34, that is, the light quantities and the light quantity ratios of the illumination light of the blue-violet laser light source 32 and the illumination light of the blue laser light source 34 can be changed.

The blue-violet laser light source 32 and the blue laser light source 34 can use a broad area type InGaN-based laser diode, and can also use an InGaNAs-based laser diode or a GaNAs-based laser diode. Additionally, the above light sources may be configured using light emitters, such as a light-emitting diode.

The laser beams irradiated from the blue-violet laser light source 32 and the blue laser light source 34 are input to optical fibers 22, respectively, by condensing lenses (not shown), and are transmitted to a connector part via a multiplexer (not shown). In addition, the invention is not limited thereto, and may have a configuration in which the laser beams from the blue-violet laser light source 32 and the blue laser light source 34 are respectively delivered directly to the connector part without using the multiplexer.

A blue-violet laser beam with a central wavelength of 405 nm and a blue laser beam with a central wavelength of 445 nm are multiplexed, and a laser beam transmitted to the connector part propagates to a distal end portion of the endoscope 12 by the optical fiber 22 which constitutes the illumination optical system. Then, the blue laser beam excites the fluorescent body 24 which is a wavelength conversion member arranged at light irradiation end of the optical fiber 22, at the distal end of the endoscope 12, thereby making the fluorescent body emit fluorescence. Additionally, a portion of the blue laser beam is transmitted through the fluorescent body 24 as it is. Although a portion of the blue-violet laser beam excites the fluorescent body 24, most of the beam is transmitted through the fluorescent body 24 without exciting the fluorescent body and becomes illumination light (so-called narrowband light) with a narrowband wavelength.

The blue-violet laser light source 32 constitutes a first light source section of the invention, and the blue laser light source 34 and the fluorescent body 24 constitute a second light source section of the invention.

The optical fiber 22 is a multimode fiber, and a fine-diameter fiber cable whose core diameter is 105 μm, cladding diameter is 125 μm, and for which a diameter including a protective layer serving as an outer skin is 0.3 to 0.5 mm can be used as an example.

The fluorescent body 24 is configured so as to include a plurality of kinds of fluorescent bodies (for example, fluorescent bodies, such as a YAG-based fluorescent body or BAM ($BaMgAl_{10}O_{17}$) fluorescent body) which absorb a portion of the blue laser beam and a portion of the blue-violet laser beam, and are excited to emit green to yellow light. Thereby, the green to yellow excitation light having the blue laser beam and the blue-violet laser beam as excitation light, and the blue laser beam and the blue-violet laser beam which are transmitted through the fluorescent body 24 without being absorbed thereby are put together, and become white (pseudo-white) illumination light. If the semiconductor light-emitting element which emits a blue laser beam with a central wavelength of 445 nm is used as an excitation light source as this configuration example, high-intensity white light can be obtained at high luminous efficiency, the intensity of the white light can be easily adjusted, and changes in color temperature and chromaticity of the white light can be suppressed to be low.

The fluorescent body 24 can prevent superposition of noise becoming an obstacle to imaging or occurrence of flickering when moving image display is performed, due to a speckle caused by the coherency of a laser beam. Additionally, the fluorescent body 24 is preferably made of a material having small absorption and large scattering of infrared light with respect to the grain sizes of the fluorescent material itself and the filler material in consideration of the refractive index difference between a fluorescent material which constitutes the fluorescent body, and a fixing and solidifying resin becoming a filler material. Thereby, a scattering effect is enhanced without reducing light intensity with respect to red light or infrared light, and optical loss becomes small.

Figure 2:
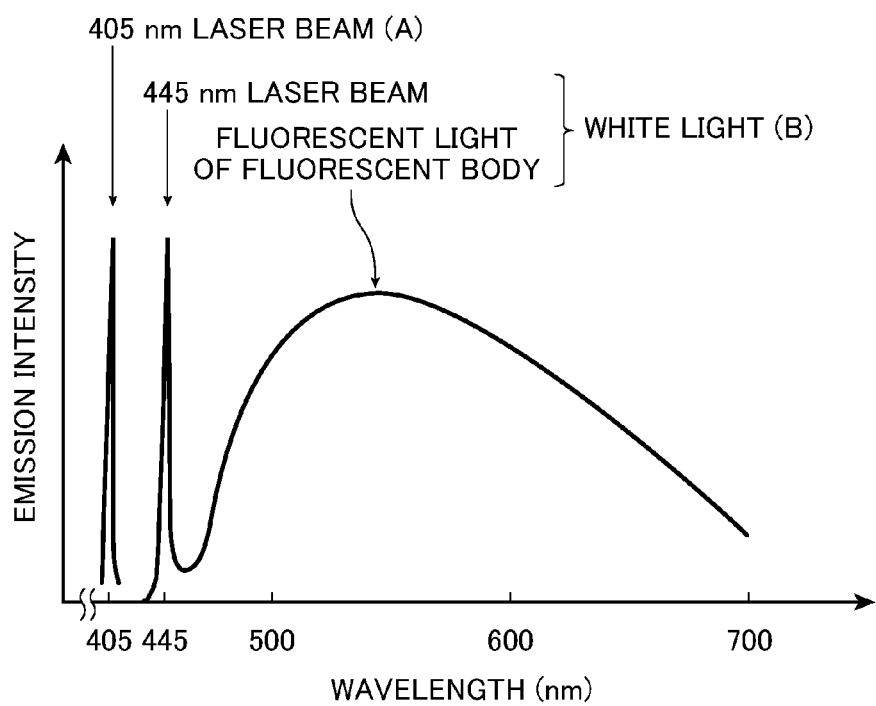
FIG. 2 is a graph showing emission spectra of a blue-violet laser beam irradiated from a blue-violet laser light source and white light from a blue laser beam irradiated from a blue laser light source and fluorescent light from an excited fluorescent body, those light sources being used for a light source section of the endoscope apparatus shown in FIG. 1.

FIG. 2 is a graph showing emission spectra of a blue-violet laser beam from the blue-violet laser light source 32 and a blue laser beam from the blue laser light source 34 combined with fluorescent light which was converted from the blue laser beam by the fluorescent body 24. The blue-violet laser beam is expressed by an emission line (profile A) with a central wavelength of 405 nm, is the narrowband light of the invention, and is used mainly as special light. Additionally, the blue laser beam is expressed by an emission line with a central wavelength of 445 nm, and fluorescent light from the fluorescent body 24 caused by the blue laser beam has a spectral intensity distribution in which emission intensity increases in a wavelength band of approximately 450 nm to 700 nm. The above-described white light is formed by a profile B including the fluorescent light and the blue laser beam, and is used mainly as normal light. The normal light which is white light is broadband light with a broad wavelength band including visible light. In addition, although not shown, the fluorescent body 24 is excited even by the blue-violet laser beam to irradiate fluorescent light with a light quantity of about 1/20 of the light quantity based on the blue laser beam, and form broadband light.

Here, there are a number of 405 nm narrowband light components in the blue-violet laser beam with a central wavelength of 405 nm emitted from the blue-violet laser light source 32 and the accompanying fluorescent light from the fluorescent body 24, and the observation (acquisition of information on a surface layer tissue) of a surface layer tissue is excellent. On the other hand, since there are few fluorescent light components from the fluorescent body 24, the irradiation light quantity of the white light used for the imaging of a background is not increased. Hence, when the distance to an object is small, the irradiation light quantity of the white light serving as a background is sufficient. However, when the distance to an object is great, the irradiation light quantity of the white light is insufficient in the fluorescent light by the blue-violet laser beam.

Additionally, although the blue laser beam with a central wavelength of 445 nm emitted from the blue laser light source 34 and the accompanying fluorescent light from the fluorescent body 24 are inferior to the blue-violet laser beam in terms of the observation of a surface layer tissue, the blue laser beam can excite the fluorescent body 24 strongly to increase the irradiation light quantity of the white light as a background. Hence, even when the distance to an object is far, the light quantity of the white light can be sufficiently secured.

Therefore, when the distance from an object is far, the blue laser light source 34 can be used in order to compensate for the shortage of the light quantity of the white light obtained from the blue-violet laser beam from the blue-violet laser light source 32.

Additionally, the white light in the invention is not strictly limited to that including all the wavelength components of visible light, for example, may include the light of a specific wavelength band, such as R, G, and B, including the above-described pseudo-white light. For example, the white light broadly includes the light including wavelength components from green to red, the light including wavelength components from blue to green, or the like.

In the endoscope apparatus 10, the emission intensity of the profile A and the profile B can be controlled so as to be relatively increased or decreased by the light source control unit 48, to produce illumination light with arbitrary luminance balance. In addition, in the endoscope apparatus 10 of the invention, only the light of the profile B is used in the normal light mode. In the special light mode, the light of the profile A and the fluorescent light (not shown) based on the light of the profile A are used in principle and the light of the profile B is superposed in order to compensate for the shortage of the light quantity of the fluorescent light which is not shown.

As described above, illumination light made up of the white light obtained from the narrowband light (profile A) based on the blue-violet laser beam from the blue-violet laser light source 32 and the fluorescent light (not shown) from the fluorescent body 24, and illumination light (profile B) made up of the white light obtained from the blue laser beam from the blue laser light source 34 and the fluorescent light from the fluorescent body 24 are irradiated toward the region of an object to be observed from the irradiation port 28A at the distal end portion of the endoscope 12. The return light from the region to be observed which is irradiated with the illumination light is focused on the light-receiving surface of the imaging element 26 via the light-receiving part 28B, and the region to be observed is imaged by the imaging element 26.

Image signals of a captured image output from the imaging element 26 after imaging are input to an image processing system 36 of the processor 16 through a scope cable 30.

Next, the image signals of the image captured by the imaging element 26 in this way are subjected to image processing by a signal processing system including the image processing system 36 of the processor 16, are output to a monitor 38 or a recording device 42, and are provided for user's observation.

Figure 3:
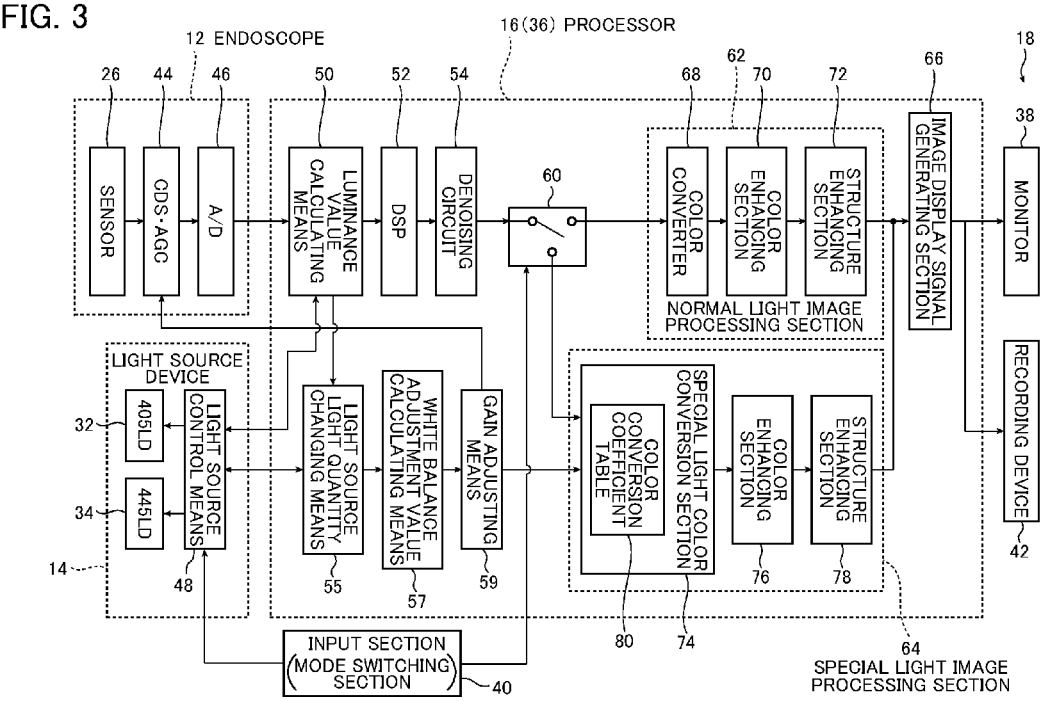
FIG. 3 is a block diagram showing signal processing systems of respective sections including the detailed configuration of one example of a processor of the endoscope apparatus shown in FIG. 1.

FIG. 3 is a block diagram showing signal processing systems of respective sections including the detailed configuration of one example of the processor of the endoscope apparatus of the invention.

As shown in this drawing, the signal processing system of the endoscope apparatus 10 has a signal processing system of the endoscope 12, a signal processing system of the light source device 14, a signal processing system of the processor 16 (image processing system 36), and the monitor 38, an input section (mode switching section) 40 and the recording device 42 of the input and output section 18.

The signal processing system of the endoscope 12 is a signal processing system for image signals of a captured image from the imaging element 26 after imaging, and has a CDS•AGC circuit 44 for performing correlated double sampling (CDS) or automatic gain control (AGC) on the captured image signals which are analog signals, and an A/D converter 46 which converts analog image signals subjected to sampling and gain control in the CDS•AGC circuit 44 into digital image signals. The digital image signals which are A/D converted in the A/D converter 46 are input to the image processing system 36 of the processor 16 via a connector part.

Additionally, the signal processing system of the light source device 14 has light source control unit 48 which performs ON/OFF control and light quantity control (intensity control) of the blue-violet laser light source 32 and the blue laser light source 34. In the invention, the light quantity includes intensity. In a first embodiment, the light source control unit 48 principally changes the irradiation intensity of a light source to change the irradiation light quantity thereof.

Here, the light source control unit 48 turns on the blue-violet laser light source 32 according to a light source ON signal accompanying the starting-up of the endoscope apparatus 10, performs ON/OFF control of the blue-violet laser light source 32 according to a switching signal between the special light mode and the normal light mode from the mode switching section 40, or controls the irradiation light quantities of the laser light sources by controlling the emission intensity of the blue-violet laser light source 32 and the blue laser light source 34, that is, the current value of driving currents sent through the blue-violet laser light source 32 and the blue laser light source 34 through the light source control unit 48 by a light source light quantity changing unit 55 so that the luminance values of the aforementioned captured image signals become predetermined luminance values, according to the luminance values of captured image information calculated from a luminance value calculating unit 50 (as will be described below). Additionally, in the invention, the predetermined luminance values mean a predetermined range of luminance values suitable for observation of a captured image.

Moreover, the signal processing system of the processor 16 is the image processing system 36 (refer to FIG. 1), and has the luminance value calculating unit 50, a DSP (digital signal processor) 52, a denoising circuit 54, the light source light quantity changing unit 55, a white balance adjustment value calculating unit 57, a gain adjusting unit 59, an image processing switching section (switch) 60, a normal light image processing section 62, a special light image processing section 64, and an image display signal generating section 66.

The luminance value calculating unit 50 calculates the light quantity of return light received in the imaging element (sensor) 26, that is, the luminance values of a captured image, using digital image signals (captured image information) input via a connector from the A/D converter 46 of the endoscope 12. Then, the calculated luminance values are output to the light source control unit 48 and the light source light quantity changing unit 55.

The light source light quantity changing unit 55 receives information on the current value of currents that drive the blue-violet laser light source 32 and the blue laser light source 34 by the light source control unit 48, and changes the irradiation light quantities and light quantity ratios of the blue-violet laser light source 32 and the blue laser light source 34 on the basis of the calculated luminance values.

For example, the instruction of reducing the irradiation light quantity of the blue laser light source 34 is issued to the light source control unit 48 so as to increase the irradiation light quantity of the blue laser light source 34 so that the blue laser beam which emits the fluorescent light to act as the white light increases if the luminance values of captured image information be small (dark) and so as to increase the ratio of the irradiation light quantity of the blue-violet laser light source 34 so that the light quantity ratios of the narrowband light is increased if the luminance values of captured image information be large (bright). Thereby, the luminance values of a captured image become predetermined luminance values suitable for observation.

Additionally, the information on the irradiation light quantities and light quantity ratios of the blue-violet laser light source 32 and the blue laser light source 34 in the light source light quantity changing unit 55 is also output to the white balance adjustment value calculating unit 57, and is output to the special light image processing section 64 through the gain adjusting unit 59.

The light source control unit 48 controls driving currents which flow into the blue-violet laser light source 32 and the blue laser light source 34, and the irradiation light quantities of the light sources, on the basis of the information on the aforementioned luminance values, and the instruction from the light source light quantity changing unit 55.

The irradiation light quantities may be controlled so as to be continuously changed according to the aforementioned luminance values, and so as to be gradually changed so that the blue-violet laser light source 32 and the blue laser light source 34 have predetermined irradiation light quantities, respectively, when the luminance values are in a predetermined range.

On the basis of the irradiation light quantities and light quantity ratios of the blue-violet laser light source 32 and the blue laser light source 34 in the light source light quantity changing unit 55, the white balance adjustment value calculating unit 57 calculates the white balances when imaging is performed with illumination light, and calculates, as white balance gains, white balance adjustment values required in order to adopt the white balances when imaging is performed with illumination light, as basis white balances.

The white balances when imaging is performed with illumination light are calculated as $[(\alpha WB\_R1+(1-\alpha)WB\_R2), (\alpha WB\_G1+(1-\alpha)WB\_G2), (\alpha WB\_B1+(1-\alpha)WB\_B2)]$, if the white balances when imaging is performed by the blue-violet laser light source 32 are [WB_R1, WB_G1, WB_B1], the white balances when imaging is performed by the blue laser light source 34 are [WB_R2, WB_G2, WB_B2], and the ratios (ratios of driving current values) between the irradiation light quantity of the blue-violet laser light source 32 and the irradiation light quantity of the blue laser light source 34 which are irradiated is $\alpha$ and $1-\alpha$, respectively.

Additionally, if the basis white balances are [WB_Rbase, WB_Gbase, WB_Bbase], the white balance gains required in order to adopt the white balances when imaging is performed with illumination light as the basis white balances can be calculated as follows:

$$WB\_gainR=(\alpha WB\_R1+(1-\alpha)WB\_R2)/WB\_Rbase$$

$$WB\_gainG=(\alpha WB\_G1+(1-\alpha)WB\_G2)/WB\_Gbase$$

$$WB\_gainB=(\alpha WB\_B1+(1-\alpha)WB\_B2)/WB\_Bbase$$

In addition, as for the white balances when imaging is performed by the blue-violet laser light source 32 and the white balances when imaging is performed by the blue laser light source 34, for example, a white plate may be installed so as to face the distal end of the endoscope before imaging of an object, the blue-violet laser light source 32 and the blue laser light source 34 may perform irradiation independently to perform imaging, and the white balances of the respective captured images (captured image information) obtained may be the white balances [WB_R1, WB_G1, WB_B1], and [WB_R2, WB_G2, WB_B2] when imaging is performed with the blue-violet laser light source 32 and the blue laser beam 34.

Additionally, as for the basis white balances, for example, similarly to the above description, a white plate may be installed so as to face the distal end of an endoscope before the imaging of an object, illumination light may be irradiated with the irradiation light quantities of the blue-violet laser light source 32 and the blue laser light source 34 being the maximum to perform imaging of the white plate, and the white balances of the captured images obtained in this case may be the basis white balances [WB_Rbase, WB_Gbase, WB_Bbase].

The white balances when imaging is performed by the blue-violet laser light source 32, the white balances when imaging is performed by the blue laser beam 34, and the basis white balances are stored in advance in the white balance adjustment value calculating unit 57.

The gain adjusting unit 59 adjusts the white balances of the captured image information in the CDS•AGC circuit 44, on the basis of the white balance gains [WB_gainR, WB_gainG, WB_gainB] calculated in the aforementioned white balance adjustment value calculating unit 57.

Additionally, the calculated white balance gains may be output to the image processing section 62 and the special light image processing section 64, and may be used for color conversion and special light color conversion.

Through the adjustment of white balances using the gain adjusting unit 59, a captured image in which white balances are always stable can be obtained even if the luminance values of the captured image have changed.

The DSP 52 (digital signal processor) performs gamma correction and color correction processing on the digital image signals output from the A/D converter 46 after the luminance values of captured image signals (captured image information) is calculated by the luminance value calculating unit 50.

The denoising circuit 54 performs a denoising method in image processing, such as a moving-average method or a median filter method, and removes noise from the digital image signals subjected to the gamma correction and color correction processing in the DSP 52.

The digital image signals input to the processor 16 from the endoscope 12 in this way are subjected to preprocessing, such as gamma correction, color correction processing, and denoising, in the DSP 52 and the denoising circuit 54.

The image processing switching section 60 is a switch which switches whether the preprocessed digital image signals are sent to the normal light image processing section 62 or the special light image processing section 64 in the subsequent stage, on the basis of the instruction (switching signal) from the mode switching section (input section) as will be described below.

In addition, in the invention, for the purpose of distinction, digital image signals before image processing using the normal light image processing section 62 and the special light image processing section 64 are referred to as an image signal, and digital image signals before and after image processing are referred to as image data.

The normal light image processing section 62 is a section which performs image processing for normal light suitable for the preprocessed digital image signals based on the white light (profile B) using the blue laser light source 34 and the fluorescent body 26, in the normal optical mode, and has a color converter 68, a color enhancing section 70, and a structure enhancing section 72.

The color converter 68 performs color conversion processing, such as matrix processing of 3×3, grayscale conversion processing, and three-dimensional LUT processing, on preprocessed RGB 3-channel digital image signals, and converts image signals into color-conversion-processed RGB image data.

The color enhancing section 70 gives a difference in tint between a blood vessel and a mucous membrane in a screen to enhance the blood vessel so as to be easily seen, and performs processing on the color-conversion-processed RGB image data while the screen is being viewed, for example, views the average tint of the full screen, and performs the processing of enhancing the tint in a direction in which the difference in tint between the blood vessel and the mucous membrane is given more than the average value.

The structure enhancing section 72 performs structure enhancement processing, such as sharpness or contour enhancement, on the color-enhanced RGB image data.

The RGB image data which has been subjected to the structure enhancement processing in the structure enhancing section 72 is input to the image display signal generating section 66 from the normal light image processing section 62 as image-processed RGB image data for normal light.

The special light image processing section 64 is a section which performs image processing for special light suitable for preprocessed digital image signals based on the blue-violet laser beam from the blue-violet laser light source 32 (profile A), and the white light (profile B) from the blue laser light source 34 and the fluorescent body 26, in the special light mode, and has a special light color conversion section 74, a color enhancing section 76, and a structure enhancing section 78.

The special light color conversion section 74 multiplies a G image signal of digital image signals of input preprocessed RGB3 channels by a predetermined coefficient to allocate the resulting value to R image data, and multiplies a B image signal by a predetermined coefficient to allocate the resulting values to B image data and G image data, respectively, thereby generating RGB image data, and then performs color conversion processing, such as 3×3 matrix processing, grayscale conversion processing, and three-dimensional LUT processing, on the generated RGB image data similarly to the color converter 68.

Specifically, the special light converter 74 normalizes luminance values with respect to the R, G, and B image data after the allocation, and generates $R_{norm}$, $G_{norm}$, and $B_{norm}$ image data. Next, the correction of the normalized $R_{norm}$, $G_{norm}$, and $B_{norm}$ image data to the color tone according to light quantity ratios is performed. If the image data after the color tone correction is $R_{adj}$, $G_{adj}$, and $B_{adj}$ image data, $R_{adj}$, $G_{adj}$, and $B_{adj}$ image data after the color tone correction are obtained by the operation as shown in Formula (1).

$$(R_{adj}, G_{adj}, B_{adj}) = (K_R, K_G, K_B)\begin{pmatrix} R_{norm} \\ G_{norm} \\ B_{norm} \end{pmatrix} \quad (1)$$

Here, $K_R$, $K_G$, and $K_B$ are color conversion coefficients of respective colors, and are obtained according to the light quantity ratios of the blue-violet laser light source 32 and the blue laser light source 34 adjusted in the light source light quantity changing unit 55. As shown in FIG. 4, the special light converter 74 includes a color conversion coefficient table 80 which determines the color conversion coefficients of respective colors corresponding to adjusted light quantity ratios, and determines the color conversion coefficients $K_R$, $K_G$, and $K_B$ from the color conversion coefficient table 80 on the basis of the aforementioned light quantity ratios. The color conversion coefficients $K_R$, $K_G$, and $K_B$ of the color conversion coefficient table 80 are set as $R_{00}$~, $G_{00}$~, and $B_{00}$~ so as to correspond to the respective light quantity ratios, as shown in FIG. 4. By substituting the color conversion coefficients corresponding to the light quantity ratios adjusted in the light source light quantity changing unit 55 into Formula (1), the image data $R_{adj}$, $G_{adj}$, and $B_{adj}$ subjected to color tone correction are obtained.

For example, when the ratio of the light quantity of the blue-violet laser light source 32 and the light quantity of the blue laser light source 34 which are controlled in the light source control unit 48 is 90:10, the color conversion coefficients are obtained as $(K_R, K_G, K_B)=(R_{10}, G_{10}, B_{10})$ by the color conversion coefficient table shown in FIG. 4.

The color conversion coefficients are not limited to those expressed as the table shown in FIG. 4, and may be expressed by a numerical formula. Additionally, only a representative point may be quantified, and other points may be obtained by interpolation operation.

The color enhancing section 76, similarly to the color enhancing section 70, gives a difference in tint between a blood vessel and a mucous membrane in a screen to enhance the blood vessel so as to be easily seen, and performs processing on the color-conversion-processed RGB image data while viewing the screen, for example, views the average tint of the full screen, and performs the processing of enhancing the tint in a direction in which the difference in tint between the blood vessel and the mucous membrane is given more than the average value.

The structure enhancing section 78, similarly to the structure enhancing section 72, performs structure processing, such as sharpness or contour enhancement, on the color-enhanced RGB image data.

The RGB image data subjected to optimal frequency enhancement processing in the structure enhancing section 78 is output to the image display signal generating section 66 from the special light image processing section 64 as image-processed RGB image data for special light.

Additionally, as mentioned above, when the light quantity is insufficient and the irradiation light quantity of the blue laser light source 34 is increased, the light quantity for imaging is sufficient. However, the color tone of a captured image changes and information on a captured image regarding the fine structure of a surface layer blood vessel observed with special light also becomes less conspicuous.

Thus, the special light image processing section 64 may perform frame addition processing or binning processing, also in order to enhance a surface layer blood vessel on a captured image, in the preceding stage of the color converter 68.

Here, the frame addition processing is generally the processing of adding a plurality of frames which generate one image in one frame, and the binning processing is the processing of unifying pixels which constitute an image in units of a plurality of pixels.

In addition, instead of the frame addition processing and binning processing, the charge storage time of the imaging element 26 may be lengthened in advance. Almost the same effect as the frame addition processing is obtained.

The image display signal generating section 66 converts the image-processed RGB image data input from the normal light image processing section 62 in the normal light mode and the image-processed RGB image data input from the special light image processing section 64 in the special light mode into display image signals for being displayed as a soft copy image in the monitor 38 or for being output as a hard copy image in the recording device 42.

The monitor 38 displays, as a soft copy image, a normal light observation image based on display image signals which are obtained in the imaging element 26 by the irradiation of white light and subjected to the preprocessing and the normal light image processing in the processor 16, in the normal light mode, and display, as a soft copy image, a special light observation image based on display image signals which are obtained in the imaging element 26 by the irradiation of special light in addition to white light and subjected to the preprocessing and the special light image processing in the processor 16, in the special light mode.

The recording device 42 also outputs the normal light observation image obtained by the irradiation of white light as a hard copy image in the normal light mode, and outputs the special light observation image obtained by the irradiation of white light and special light as a hard copy image in the special light mode.

In addition, if required, the display image signals generated in the image display signal generating section 66 may be stored as image information in a storage section made up of memory or a storage device, though not shown.

On the other hand, the mode switching section (input section) 40 has mode switching buttons for performing switching between the normal light mode and the special light mode, and a mode switching signal from the mode switching section 40 is input to the light source control unit 48 of the light source device 14. Here, although the mode switching section 40 is arranged as the input section 40 of the input and output section 18, the mode switching section may be arranged at the processor 16, the manipulation part of the endoscope 12, or the light source device 14. In addition, a switching signal from the mode switching section 40 is output to the light source control unit 48 and the image processing switching section 60.

The endoscope apparatus 10 of the first embodiment of the invention is basically configured as described above.

Next, the operation of the endoscope apparatus 10 of the first embodiment of the invention will be described with reference to FIG. 5.

In the present embodiment, first, normal light observation shall be performed in the normal light mode. That is, the blue laser light source 34 is turned on, and normal light image processing is performed on captured image data based on white light in the normal light image processing section 64.

Figure 5:
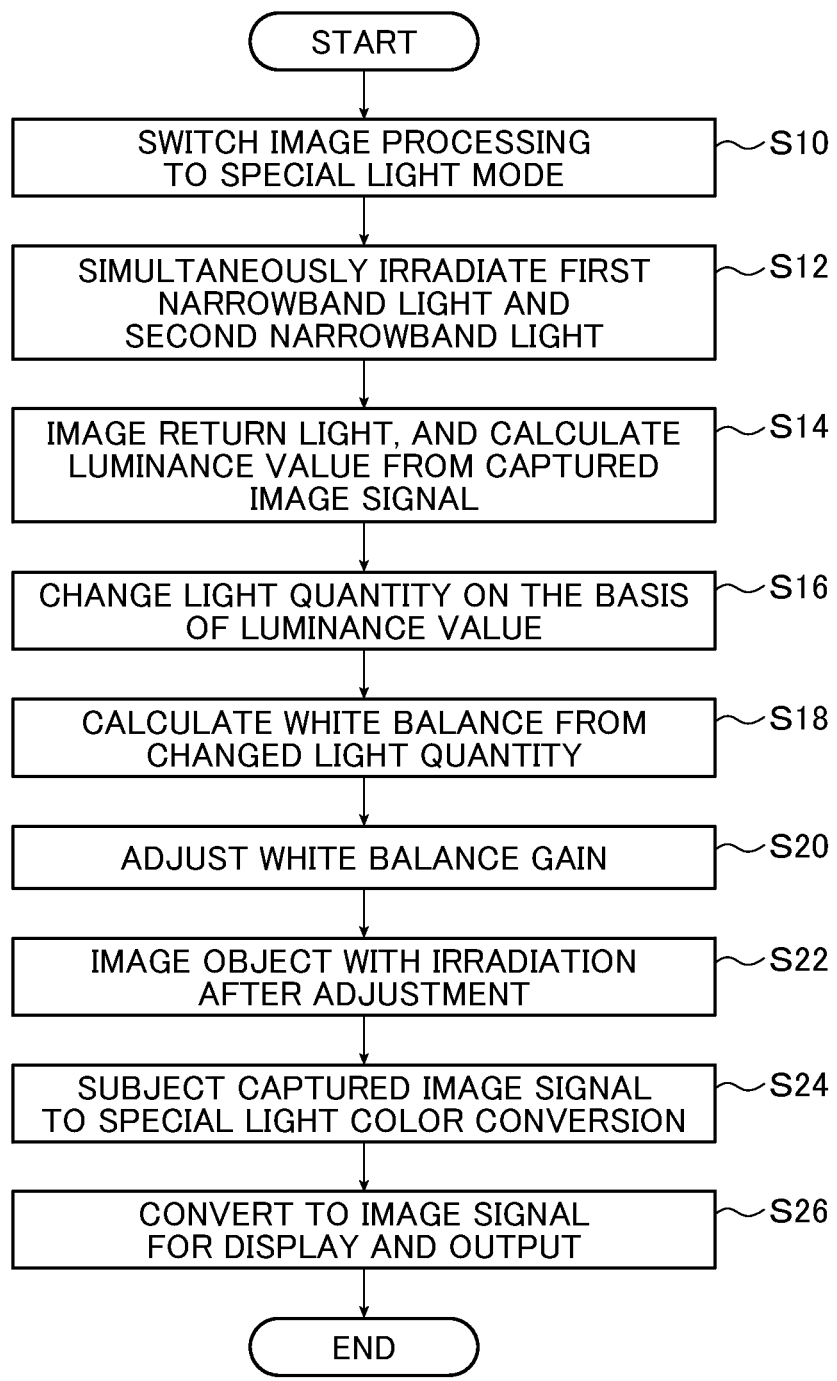
FIG. 5 is a flowchart showing an example of the operation of the first embodiment of the endoscope apparatus of the invention.

Here, switching to the special light mode is performed by a user according to the steps shown in FIG. 5. A mode switching signal (special light ON) is output as the user operates the mode switching section 40, and the image processing in the image processing switching section 60 is switched to the special light mode. Additionally, switching to the special light mode may be performed not by operating the mode switching section 40 but by operating the manipulation part (not shown) of the aforementioned endoscope 12 (S10).

When switching to the special light mode is performed, a predetermined quantity of the first narrowband light (with a central wavelength of 405 nm) from the blue-violet laser light source 32, and a predetermined quantity of the second narrowband light (with a central wavelength of 445 nm) from the blue laser light source 34 are simultaneously irradiated, and the first narrowband light, the second narrowband light, and the fluorescent light are irradiated toward an object from the distal end of the endoscope as illumination light (S12).

The irradiated illumination light is reflected by the object, the return light is acquired by the imaging element 26 as captured image signals (captured image information), and the luminance values of the captured image signals acquired by the imaging element 26 are calculated in the luminance value calculating unit 50. The luminance values of the calculated captured image signals are output to the light source light quantity changing unit 55 and the light source control unit 48 (S14).

Then, the light source light quantity changing unit 55 adjusts the respective irradiation light quantities of the blue-violet laser light source 32 and the blue laser light source 34 and adjusts the light quantity ratios thereof so that the captured image is not too bright and is not too dark and the luminance values become predetermined luminance values, on the basis of the information on the luminance values calculated in the luminance value calculating unit 50 and the information on the irradiation light quantities and light quantity ratios from the blue-violet laser light source 32 and the blue laser light source 34 obtained from the light source control unit 48. These adjustments are performed in practice by adjusting the values of driving currents which flows to the blue-violet laser light source 32 and the blue laser light source 34 through the light source control unit 48. Then, the information on the adjusted irradiation light quantities and light quantity ratios is output to the light source control unit 48 and the white balance adjustment value calculating unit 57, respectively (S16).

Since Step S14 and Step S16 are performed according to changes in the luminance values, these steps are performed according to a change in the positional relationship between the distal end of the endoscope and the object.

Additionally, the white balance adjustment value calculating unit 57 first calculates the white balances of the captured image on the basis of the information on the aforementioned adjusted irradiation light quantities and light quantity ratios. The white balances, as mentioned above, are calculated on the basis of the white balances of the illumination light based on the blue-violet laser light source 32, the white balances of the illumination light based on the blue laser light source 34, and the irradiation light quantities and light quantity ratios of the blue-violet laser beam and the blue laser beam (S18).

Then, white balance gains required in order to maintain the white balances are calculated from the calculated white balances and the basis white balances, and the white balance gains are adjusted in the CDS•AGC circuit 44 through the gain adjusting unit 59 (S20).

After the irradiation light quantities and light quantity ratios from the blue-violet laser light source 32 and the blue laser light source 34 is changed by the light source light quantity changing unit 55, and the white balance gains are adjusted by the gain adjusting unit 59, imaging of an object is performed and captured image signals are acquired by the imaging element 26 (S22).

If captured image signals are acquired again, the captured image signals are output to the luminance value calculating unit 50 through the CDS•AGC 44 and the A/D converter 46, and the luminance values of the captured image (signals) are calculated. Thereafter, the captured image signals are output to the special light image processing section 64 through the DSP52 and the denoising circuit 54. In the special light color conversion section 74 of the special light image processing section 64, the color conversion coefficients $K_R$, $K_G$, and $K_B$ used for special light color conversion, are set from the information on the aforementioned changed irradiation light quantities and light quantity ratios, and the color conversion coefficient table 80, and the captured image signals input to the special light image processing section 64 are turned into predetermined RGB image data by the special light color conversion section 74. In addition, image enhancement processing such as frame addition processing or the like may be performed before the special light color conversion. Additionally, the RGB image data is subjected to various image processing in the color enhancing section 76 and the structure enhancing section 78, and is output to the image display signal generating section 66 (S24).

The RGB image data output to the image display signal generating section 66 is converted into image display signals which can be displayed, is displayed on the monitor 38 as a special light image, and is recorded in the recording device 42 (S26).

Figure 6:
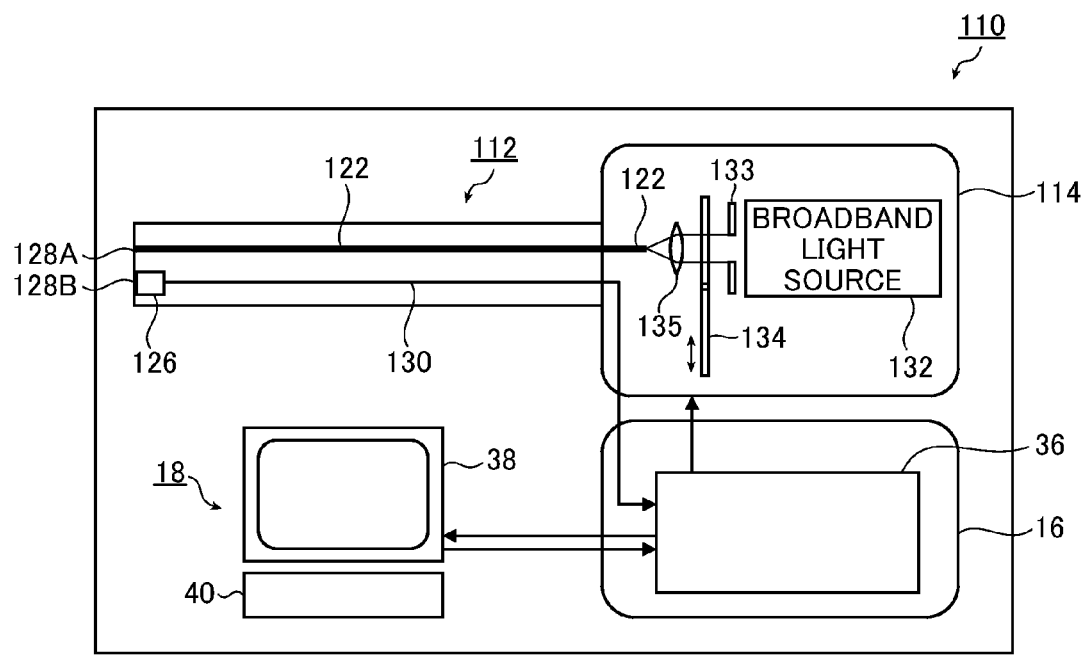
FIG. 6 is a block diagram schematically showing the overall configuration of a second embodiment of the endoscope apparatus of the invention.

The above is the first embodiment of the invention. Next, a second embodiment of the invention will be described. FIG. 6 is a block diagram schematically showing the overall configuration of a second embodiment of the endoscope apparatus of the invention.

As shown in FIG. 6, the constitutional differences between the second embodiment and the first embodiment are the configuration of the light source device 114, and the fluorescent body 24 installed at the distal end of the endoscope 112 in the first embodiment which is unnecessary in the second embodiment. Hence, the differences from the first embodiment will be described.

As mentioned above, the endoscope 112 of FIG. 6 is the same as the endoscope 12 of the first embodiment except that the fluorescent body 24 is not present at the distal end of the endoscope. Hence, an optical fiber 112 is the same as the optical fiber 22, an irradiation port 128A is the same as the irradiation port 28A, a light-receiving part 128B is the same as the light-receiving part 28B, an imaging element 126 is the same as the imaging element 26, and a scope cable 130 is the same as the scope cable 30, and these components perform the same operations, respectively.

Additionally, as shown in FIG. 6, a light source device 114 includes a broadband light source 132, a light quantity diaphragm 133, a filter set 134 including a first color filter 134B and a second color filter 134G, and a condensing lens 135. Additionally, the light source device 114 forms a first light source section by the combination of the broadband light source 132 and the first color filter 134B, and forms a second light source section by the combination of the broadband light source 132 and the second color filter 134G. The broadband light source 132 is, for example, a xenon light source which irradiates xenon light, for example, and irradiates predetermined broadband light (white light).

Additionally, the broadband light source 132 performs light quantity adjustment using the light quantity diaphragm 133. Since adjustment of the emission intensity of the broadband light source 132 is difficult unlike the laser light source in the first embodiment, light quantity is adjusted by the light quantity diaphragm. Accordingly, the emission intensity of the broadband light source 132 is constant in principle.

In addition, in the present embodiment, xenon light is used as the broadband light, and a xenon light source is used as the broadband light source 132. However, in the invention, the light source is not particularly limited if a light source which irradiates white illumination light capable of being band-narrowed using the first color filter and the second color filter is adopted. In addition to the xenon light source, discharge tubes including discharge-type high-luminance lamp light sources, such as a mercury lamp or a metal halide lamp, can be used.

Additionally, a white light source in which a laser light source and a fluorescent body are combined together can also be used. In this case, since the emission intensity can be adjusted depending on the driving current value of the laser light source unlike the above description, the light quantity diaphragm 133 is unnecessary.

After irradiated broadband light is turned into a substantially parallel pencil by a reflector (not shown) which is a convergence optical system and the light quantity thereof is adjusted by the light quantity diaphragm 133, the light is transmitted through a predetermined filter of the filter set 134.

The narrow-banded light which is transmitted through the first color filter 134B and the second color filter 134G is condensed at an incidence end of the optical fiber 112 by the condensing lens 135, and enters the optical fiber 112. The entered light is guided by the optical fiber 112 and irradiated from the distal end of the endoscope.

The broadband light transmitted through the first color filter 134B is irradiated from the distal end of the endoscope as the first narrowband light, and the broadband light transmitted through the second color filter 134B is emitted from the distal end of the endoscope as the second narrowband light.

Figure 7:
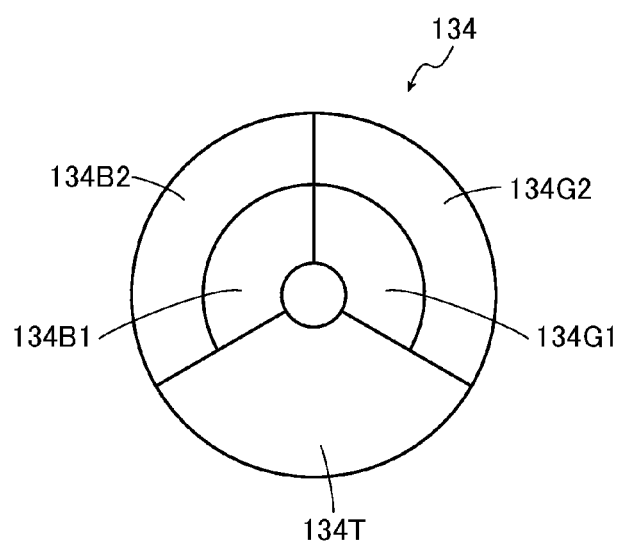
FIG. 7 is a front view showing one example of a filter set including first and second color filters of the endoscope apparatus shown in FIG. 6.

The filter set 134, as shown in FIG. 7, is made up of the first color filter 134B which converts broadband light into blue narrowband light (B light or first narrowband light), the second color filter 134G which converts broadband light into green narrowband light (G light or second narrowband light), and a transmission part 134T which allows broadband light to be transmitted therethrough as it is. Additionally, the first color filter 134B is made up of a blue filter 134B1 with a narrow half-value width, and a blue filter 134B2 with a wide half-value width, and the second color filter 134G is made up of a green filter 134G1 with a narrow half-value width, and a green filter 134G2 with a wide half-value width. The filter set 134 is switched by a moving unit and a rotating unit (not shown) according to an instruction from a light source control unit 148 (refer to FIG. 9).

FIG. 8A is a graph showing an example of the spectral characteristics of the blue filter 134B1 with a narrow half-value width and the green filter 134G1 with a narrow half-value width, and FIG. 8B is a graph showing an example of the spectral characteristics of the blue filter 134B2 with a wide half-value width, and the green filter 134G2 with a wide half-value width.

When the light quantity is insufficient even if the light quantity diaphragm 133 is opened to the maximum, thereby maximizing the irradiation light quantity, the irradiation light quantity can be further increased by performing switching from the filter with a narrow half-value width to the filter with a wide half-value width as mentioned above.

Figure 9:
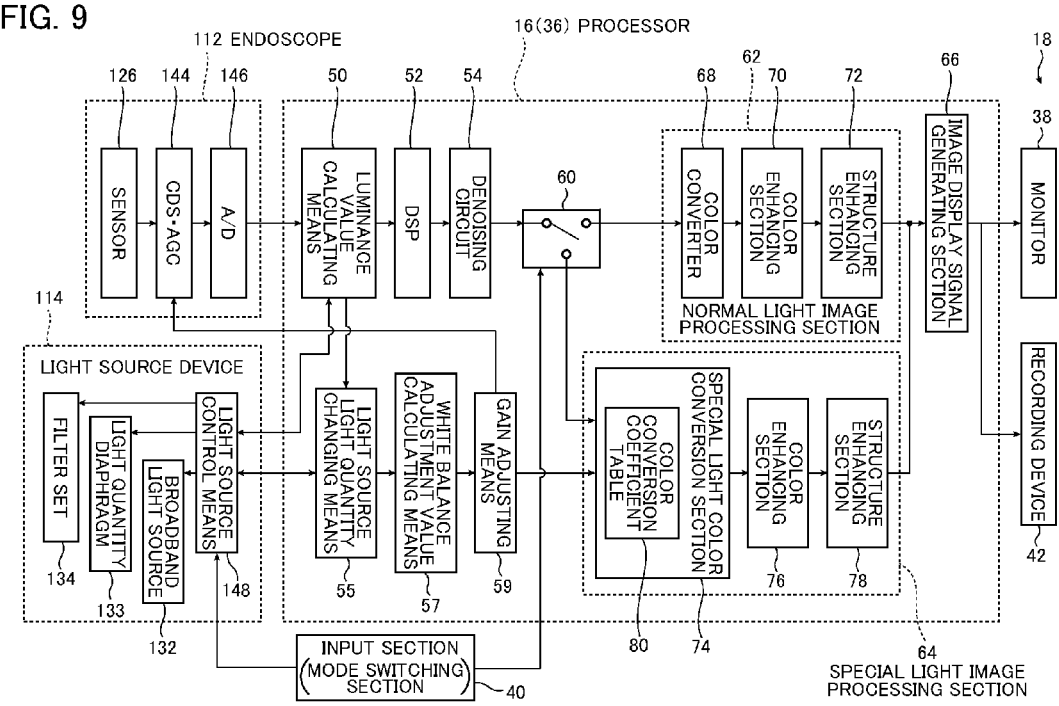
FIG. 9 is a block diagram showing signal processing systems of respective sections including the detailed configuration of one example of a processor of the endoscope apparatus shown in FIG. 6.

FIG. 9 is a block diagram showing signal processing systems of respective sections including the detailed configuration of the processor of the second embodiment of the endoscope apparatus of the invention. The difference from FIG. 3 of the first embodiment shown in FIG. 3 is the light source device 114. In addition, since the difference between the endoscope 112 and the endoscope 12 is only the fluorescent body 24, there is no constitutional difference in the block diagram showing the signal processing system of FIG. 9.

Accordingly, similarly to the above description, the light source device 114 which is the difference from the first embodiment will be described.

The signal processing system of the light source device 114 has the light source control unit 148 which performs ON/OFF control of the broadband light source 132, light quantity control using the light quantity diaphragm 133, switching control from the filters 134B1 and 134G1 with a narrow half-value width to the filters 134B2 and 134G2 with a wide half-value width using the moving unit (not shown), and switching control of the first color filter 134B, the second color filter 134G, and the transmission part 134T using the rotating unit (not shown).

Here, the light source control unit 148 turns on the broadband light source 132 according to a light source ON signal accompanying the starting-up of the endoscope apparatus 10, the controls switching between the transmission part 134T, and the first color filter 134B and the second color filter 134G of the filter set 134 according to a switching signal between the normal light mode and the special light mode from the mode switching section 40, controls the light quantity of broadband light, that is, the light quantity diaphragm 133 through the light source control unit 148, using the light source light quantity changing unit 55, thereby controlling the irradiation light quantity from the broadband light source 132, so that the luminance values of the aforementioned captured image signals become predetermined luminance values according to the luminance values of captured image information calculated from the luminance value calculating unit 50, and performs switching of the filter set 134 from the filters 134B1 and 134G1 with a narrow half-value width to the filters 134B2 and 134G2 with a wide half-value width, thereby controlling the irradiation light quantities thereof.

The light source light quantity changing unit 55 switches the blue filter 134B1 with a narrow half-value width and the green filter 134G1 with a narrow half-value width in the first color filter 134B and the second color filter 134G to the blue filter 134B2 with a wide half-value width and the green filter 134G2 with a wide half-value width, on the basis of the information on the light quantity diaphragm 133 using the light source control unit 148, the information on installed filters of the filter set 134, and the calculated luminance values. Here, the installed filters mean filters which allow broadband light to be transmitted therethrough in practice. Additionally, the information on the installed filters is information on whether any filters of the aforementioned filters 134B1, 134B2, 134G1, and 134G2, and the transmission part 134T are selected as the installed filters.

For example, when there is no need to raise the luminance values of a captured image and the irradiation light quantities are sufficient, it is not necessary to raise the irradiation light quantities to a fixed value or more. Therefore, the filters 134B1 and 134G1 with a narrow half-value width are sufficient. When it is necessary to raise the luminance values of a captured image and it is necessary to raise the irradiation light quantities to a fixed value or more, there is a limit to the light quantities which can be transmitted through a filter with a narrow half-value width. Therefore, an instruction for switching of the first color filter 134B and the second color filter 134G is issued to the light source control unit 148 so that switching to the filters 134B2 and 134G2 with a wide half-value width from the filters 134B1 and 134G1 with a narrow half-value width is performed. Thereby, the luminance values of a captured image become predetermined luminance values suitable for observation. In addition, the aforementioned fixed value means the irradiation light quantity when the light quantity diaphragm 133 is maximized using the filters 134B1 and 134G1 with a narrow half-value width as the installed filters.

Additionally, the information on the light quantity diaphragm 133 of the broadband light source 132 in the light source light quantity changing unit 55 and the information on the installed filters of the filter set 134 are also output to the white balance adjustment value calculating unit 57.

The light source control unit 148 controls the light quantity diaphragm 133 on the basis of the information on the aforementioned luminance values, and an instruction from the light source light quantity changing unit 55, thereby controlling the irradiation light quantity from the broadband light source 132, and switches the installed filters from the filters B1 and G1 with a narrow half-value width of the filter set 134 to the filter B2 and G2 with a wide half-value width, thereby controlling the irradiation light quantities.

On the basis of the irradiation light quantity of broadband light in the light source light quantity changing unit 55, and the information on the installed filters of the filter set 134, the white balance adjustment value calculating unit 57 calculates the white balances when imaging is performed with illumination light, and calculates, as white balance gains, white balance adjustment values required in order to adopt the white balances when imaging is performed with illumination light, as basis white balances.

Depending on whether broadband light has been transmitted through any filter of the blue filter 134B1 with a narrow half-value width, the blue filter 134B2 with a wide half-value width, the green filter 134G1 with a narrow half-value width, and the green filter 134G2 with a wide half-value width, the wavelength profile of the narrowband light after the transmission is determined as shown in FIGS. 8A and 8B.

Hence, it turns out that the white balances are uniquely determined in advance depending on the irradiation light quantities of the broadband light which is transmitted through the aforementioned filters 134B1, 134B2, 134G1, and 134G2.

The white balance adjustment value calculating unit 57 of FIG. 9 includes a white balance table (not shown) recorded by measuring the relationship between irradiation light quantity and white balance with respect to the type of installed filters in advance, and calculates the white balances of captured image information, using the white balance table from the information on the irradiation light quantity of the broadband light output from the light quantity changing unit 55 and the information on the installed filters.

Additionally, as for the basis white balances, the white balances of a captured image when imaging is performed using the filters B1 and G1 with a narrow half-value width may be adopted as the basis white balances.

The reason why the white balances have collapsed is that the filters B2 and G2 with a wide half-value width are used since light quantity is insufficient, and that there is no necessity for gain adjustment when light quantity is sufficient if the white balances of a captured image when captured image information is acquired using the filters B1 and G1 with a narrow half-value width as the installed filters are adopted as the basis white balances.

The white balance adjustment value calculating unit 57 calculates white balance gains as white balance adjustment values for adjusting the calculated white balances to the basis white balances, and outputs the gains to the gain adjusting unit 59.

When imaging is performed using the filters B2 and G2 with a wide half-value width as the installed filters, as mentioned above, the gain adjusting unit 59 is used in order to adjust the white balances of captured image signals to the white balances when the filters B1 and G2 with a narrow half-value width are used as the installed filters.

In the gain adjusting unit 59, a B image signal including a B light image component and a G image signal including a G light image component in which the white balances of the captured image signals are adjusted are output to the special light image processing section 64, respectively, and are synthesized into one image data. Specifically, the synthesis of the image data is performed by allocating the G image signal to R image data, and allocating the B image signal to B image data and G image data similarly to the image processing performed in the aforementioned special light image processing section 64. The processing except for synthesizing one item of image data from the B image signal and G image signal imaged in two frames is the same as that of the first embodiment.

In addition, in the second embodiment, in the special light color conversion section 74, the irradiation light quantity from the broadband light source 132 and the information on the installed filters are used instead of the information on the changed irradiation light quantities and light quantity ratios that are used in the first embodiment. This is because the light quantity ratios in the first embodiment, that is, the ratio between R light component, G light component, and B light component of illumination light can be calculated depending on the information on the irradiation light quantities and the installed filters.

The configuration other than the above description is the same as that of the first embodiment. The second embodiment of the endoscope apparatus of the invention is basically configured as described above.

Next, the operation of the second embodiment of the endoscope apparatus 110 of the invention will be described with reference to the flowchart of FIG. 10. The description of the same operation as in the first embodiment is omitted partially, and differences will be mainly described.

Even in the present embodiment, first, normal light observation shall be performed in the normal light mode. That is, the transmission part 134T is installed as the installed filter, the broadband light source is turned on, and normal light image processing is performed on captured image data based on broadband light in the normal light image processing section 64.

Figure 10:
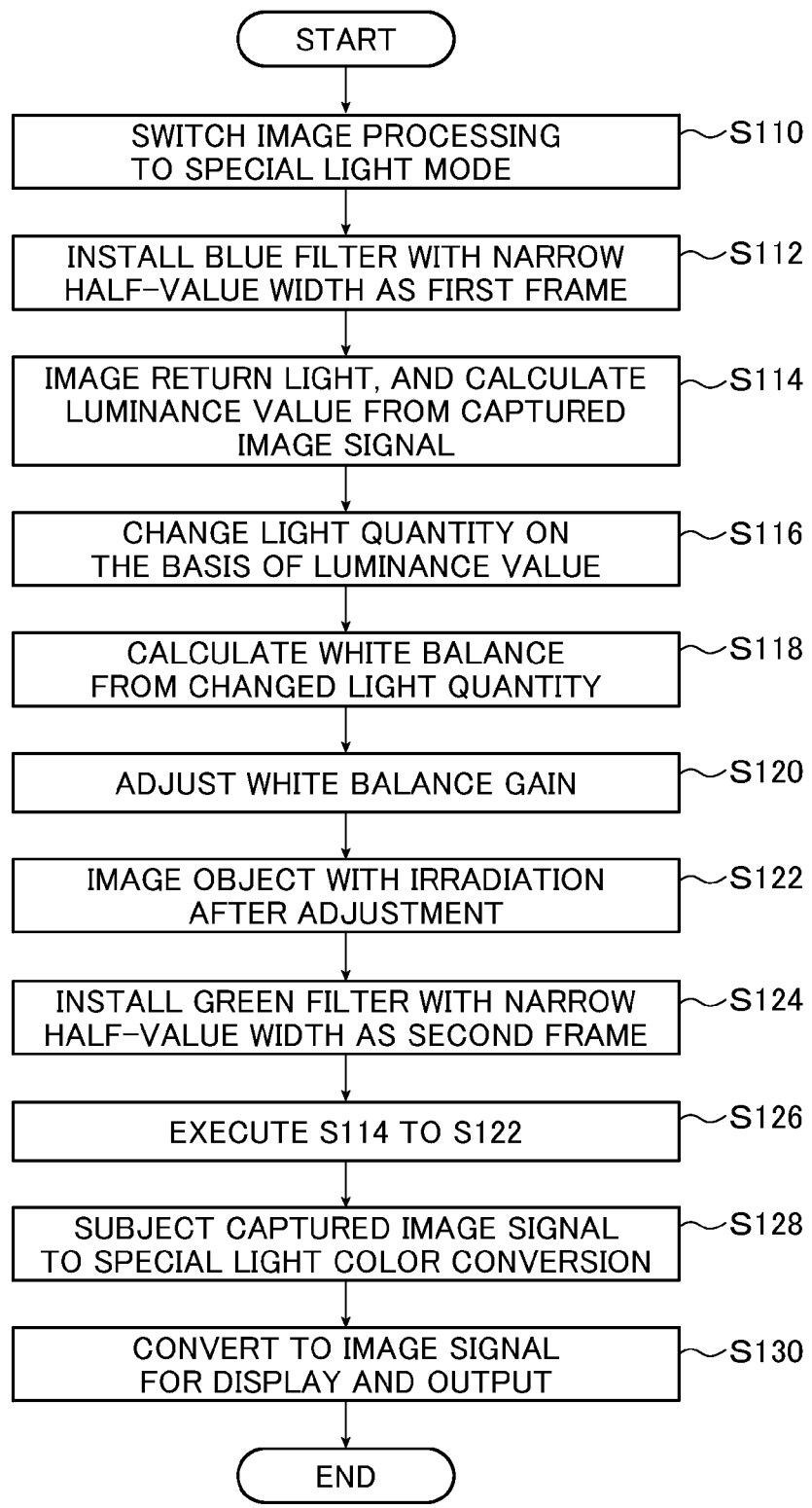
FIG. 10 is a flowchart showing an example of the operation of the second embodiment of the endoscope apparatus of the invention.

Here, switching to the special light mode is performed by a user according to the steps shown in FIG. 10 (S110). The second embodiment adopts the face sequential system which images B image data and G image data in two frames in the special light imaging in terms of the configuration thereof.

If switching to the special light mode is made, first, the blue filter 134B1 with a narrow half-value width is installed as the installed filter in a first frame. Then, broadband light is emitted from the broadband light source 132, and the irradiation light quantity thereof is adjusted by the light quantity diaphragm 133, whereby a predetermined light quantity of broadband light is turned into the first narrowband light through the blue filter 134B1 with a narrow half-value width, and is irradiated toward an object from the distal end of the endoscope (S112).

The irradiated first narrowband light is reflected by the object, the return light is acquired by the imaging element 126 as captured image signals (captured image information), and the luminance values of the captured image signals acquired by the imaging element 126 are calculated in the luminance value calculating unit 50. The luminance values of the calculated captured image signals are output to the light source light quantity changing unit 55 and the light source control unit 148 (S114).

Then, the light source light quantity changing unit 55 adjusts the light quantity of the light quantity diaphragm 133 to change the irradiation light quantity of the broadband light source 132 so that the captured image is not too bright and is not too dark and the luminance values become predetermined luminance values, on the basis of the information on the luminance values calculated in the luminance value calculating unit 50, the information on the light quantity of broadband light controlled from the light source control unit 148, that is, the information of the light quantity diaphragm 133 and the information of the installed filters, and changes the installed filters from the filters with a narrow half-value width to the filters with a wide half-value width to change the irradiation light quantities when the irradiation light quantities are insufficient. Then, the information on the changed irradiation light quantities and installed filters is output to the light source control unit 148 and the white balance adjustment value calculating unit 57, respectively (S116).

Since Step S114 and Step S116 are performed according to changes in the luminance values, these steps are performed according to a change in the positional relationship between the distal end of the endoscope and the object.

Additionally, the white balance adjustment value calculating unit 57 calculates the white balances of the captured image on the basis of the information on the aforementioned changed irradiation light quantities and installed filters. The white balances is calculated on the basis of the irradiation light quantity of broadband light, the information on the installed filters, and the white balance table (not shown) as mentioned above (S118).

Then, white balance gains required in order to maintain the white balances are calculated from the calculated white balances and the basis white balances, and the white balance gains are adjusted in the CDS•AGC circuit 44 through the gain adjusting unit 59 (S120).

After the irradiation light quantity from the broadband light source 132 and the installed filters are changed by the light source light quantity changing unit 55, and the white balance gains are adjusted by the gain adjusting unit 59, imaging of an object is performed and a captured image signal (B image signal) of the first frame is acquired by the imaging element 26 (S122). The acquired B image signal is temporarily stored in the special light image processing section 64.

Next, in the second frame, the installed filter is switched to the green filter 134G1 with a narrow half-value width (S124).

If the installed filter is switched, previous steps S114 to S124 are repeatedly performed, and a captured image signal (G image signal) of the second frame is acquired (S126). The acquired G image signal is stored in the special light image processing section 64 similarly to the first frame.

The B image signal and the G image signal which are temporarily stored in the special light image processing section 64 are synthesized into one item of RGB image data. Similarly to Step S24, the RGB image data is synthesized by allocating the G image signal to R image data, and allocating the B image signal to B image data and G image data. The RGB image data is subjected to various processing similarly to Step S24, and is output to the image display signal generating section 66 (S128).

Similarly to Step S26, the RGB image data output to the image display signal generating section 66 is converted into image display signals which can be displayed, is displayed on the monitor 38 as a special light image, and is recorded in the recording device 42 (S130).

In this way, an image component of B light and an image component of G light which are white-balanced can be acquired, respectively, as the first frame and the second frame are alternately repeated. A special light captured image is obtained by synthesizing the image component of B light and the image component of G light which are imaged in this way in the special light image processing section 64.

The above is the second embodiment of the invention.

Although the endoscope apparatus of the invention has been described in detail above, the invention is not limited to the above embodiments, and various improvements and modifications may be performed without departing from the scope of the invention.

What is claimed is:

1. An endoscope apparatus comprising:
a first light source section that irradiates first narrowband light with a predetermined wavelength bandwidth narrow-banded according to the spectral characteristics of the structure or components of a living body used as an object;
a second light source section that irradiates second narrowband light with a wavelength band different from the first narrowband light or broadband light with a broad wavelength band including visible light;
a light source control unit which controls the irradiation and irradiation light quantity of the first narrowband light from the first light source section, and the irradiation and irradiation light quantity of the second narrowband light or broadband light from the second light source section, respectively;
an imaging unit which obtains a captured image of the object to output captured image information, using return light from the object, of the first narrowband light and the second narrowband light or broadband light sequentially or simultaneously irradiated to the object;
a luminance value calculating unit which calculates the luminance value of the captured image from the captured image information imaged by the imaging unit;
a light source light quantity changing unit which changes the irradiation light quantity of the first narrowband light from the first light source section, and the irradiation light quantity of the second narrowband light or broadband light from the second light source section, according to the luminance value calculated in the luminance value calculating unit;
a white balance adjustment value calculating unit which calculates a white balance adjustment value for taking the white balance of the captured image from the irradiation light quantities, changed in the light source light quantity changing unit, of the first light source section and the second light source section which perform irradiation currently;
a gain adjusting unit which adjusts a gain of the imaging unit so that the white balance of the captured image becomes a basis white balance according to the white balance adjustment value calculated in the white balance adjustment value calculating unit; and
an image processing section which performs predetermined image processing on the captured image information,
wherein the image processing section has a color conversion coefficient table showing the relationship between the ratio of the irradiation light quantity of the first light source section and the irradiation light quantity of the second light source section which are obtained in advance, and a color conversion coefficient for adjusting the tint of the captured image so that image processing is performed, and thereby, the white balance of the captured image does not change, and
wherein the image processing section selects the color conversion coefficient from the color conversion coefficient table on the basis of the ratio of the irradiation light quantity of the first light source section and the irradiation light quantity of the second light source section adjusted by the light source light quantity changing unit.

2. The endoscope apparatus according to claim 1,
wherein the basis white balance is a white balance of the captured image obtained when a white plate is imaged with the irradiation light quantity of the first light source section and the irradiation light quantity of the second light source section being maximized, respectively.

3. The endoscope apparatus according to claim 1,
wherein the light source light quantity changing unit is the unit which changes the ratio of the irradiation light quantity of the first narrowband light from the first light source section and the irradiation light quantity of the second narrowband light from the second light source section.

4. The endoscope apparatus according to claim 3,
wherein the light source light quantity changing unit increases the ratio of the irradiation light quantity from the first light source section as the calculated luminance value becomes large, and increases the ratio of the irradiation light quantity from the second light source section as the calculated luminance value becomes small, thereby setting the calculated luminance value to a predetermined luminance value.

5. The endoscope apparatus according to claim 1,
wherein the light source light quantity changing unit is the unit which changes the ratio of the irradiation light quantity of the first narrowband light from the first light source section and the irradiation light quantity of the broadband light from the second light source section.

6. The endoscope apparatus according to claim 1,
wherein the light source light quantity changing unit gradually changes the irradiation light quantity of the first narrowband light from the first light source section according to the luminance value of the captured image.

7. The endoscope apparatus according to claim 1,
wherein the light source light quantity changing unit continuously changes the irradiation light quantity of the first narrowband light from the first light source section according to the luminance value of the captured image.

8. The endoscope apparatus according to claim 1,
wherein if the basis white balances are [R_base, G_base, B_base], the ratio of the irradiation light quantity of the first light source section and the irradiation light quantity of the second light source section is $\alpha:1-\alpha$, the white balances of the first light source section are [R_1, G_1, B_1], and the white balances of the second light source section are [R_2, G_2, B_2], the gains [WB_gainR, WB_gainG, WB_gainB] of the imaging element adjusted by the gain adjusting unit are expressed by the following formulas $$WB\_gainR = (\alpha R\_1 + (1-\alpha)R\_2)/R\_base$$

$$WB\_gainG = (\alpha G\_1 + (1-\alpha)G\_2)/G\_base$$

$$WB\_gainB = (\alpha B\_1 + (1-\alpha)B\_2)/B\_base.$$

9. The endoscope apparatus according to claim 1,
wherein the first light source section includes a broadband light source which emits broadband light, and a first color filter which transmits only the first narrowband light from the broadband light emitted from the broadband light source,
wherein the second light source section includes the broadband light source, and a second color filter that transmits only the second narrowband light from the broadband light emitted from this broadband light source, and
wherein the light source light quantity changing unit is the unit which switches at least one of the first color filter and the second color filter to a color filter with a different half-value width.

* * * * *